United States Patent [19]

Fleisher

[11] 4,333,734

[45] Jun. 8, 1982

[54] DIAGNOSTIC DEVICE FOR FECAL OCCULT BLOOD AND METHOD OF USE

[75] Inventor: Martin Fleisher, Glen Cove, N.Y.

[73] Assignee: Sloan-Kettering Institute for Cancer Research, New York, N.Y.

[21] Appl. No.: 195,220

[22] Filed: Oct. 8, 1980

Related U.S. Application Data

[63] Continuation-in-part of Ser. No. 113,414, Jan. 18, 1980, abandoned.

[51] Int. Cl.$^3$ .................... G01N 21/78; G01N 33/72
[52] U.S. Cl. .................... 23/230 B; 23/931; 252/408; 422/56; 422/61; 435/184
[58] Field of Search ............ 23/931, 230 B, 932; 435/4, 28, 184; 422/56, 61; 252/408

[56] References Cited

U.S. PATENT DOCUMENTS 2,905,594 9/1959 Morris .................................. 435/28
2,990,338 6/1961 Gibson ............................... 422/56 X
3,917,452 11/1975 Rittersdorf et al. ............ 252/408 X
3,996,006 12/1976 Pagano ............................. 422/58 X
4,017,261 4/1977 Svoboda et al. ............... 23/230 B X

OTHER PUBLICATIONS

Henry, "Clinical Chemistry—Principles and Techniques", Harper and Row, 1964, New York, pp. 78-785.
Mahler et al., "Biological Chemistry", Harper and Row, New York, 1966, pp. 117-120.

Primary Examiner—Arnold Turk
Attorney, Agent, or Firm—Felfe & Lynch

[57] ABSTRACT

Diagnostic test device for fecal occult blood utilizing a test matrix such as paper impregnated with guaiac. False-positive results in the presence of peroxidases are prevented by adding to the matrix a compound that cleaves protein hydrogen bonds such as guanidine hydrochloride and a chelating agent that binds calcium and/or magnesium such as EDTA.

12 Claims, 3 Drawing Figures

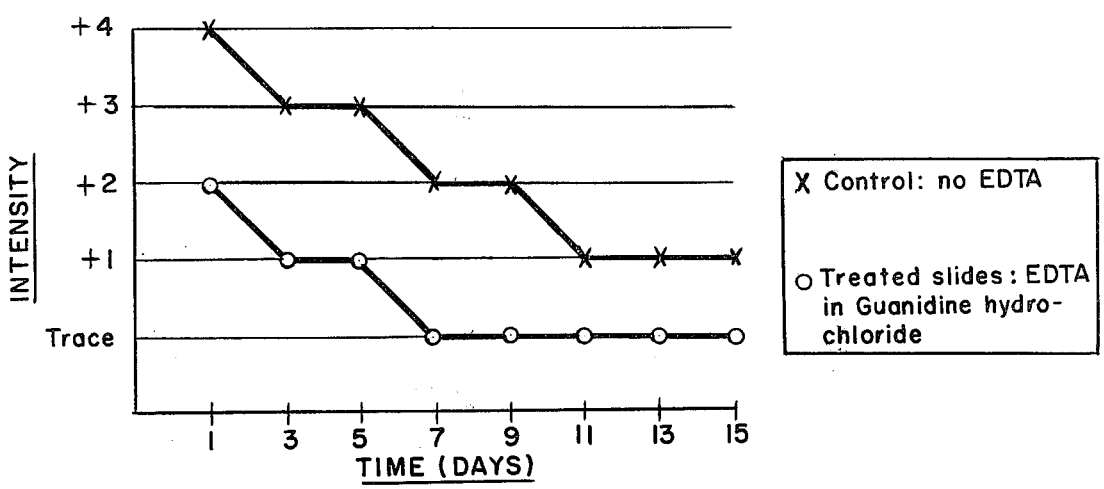
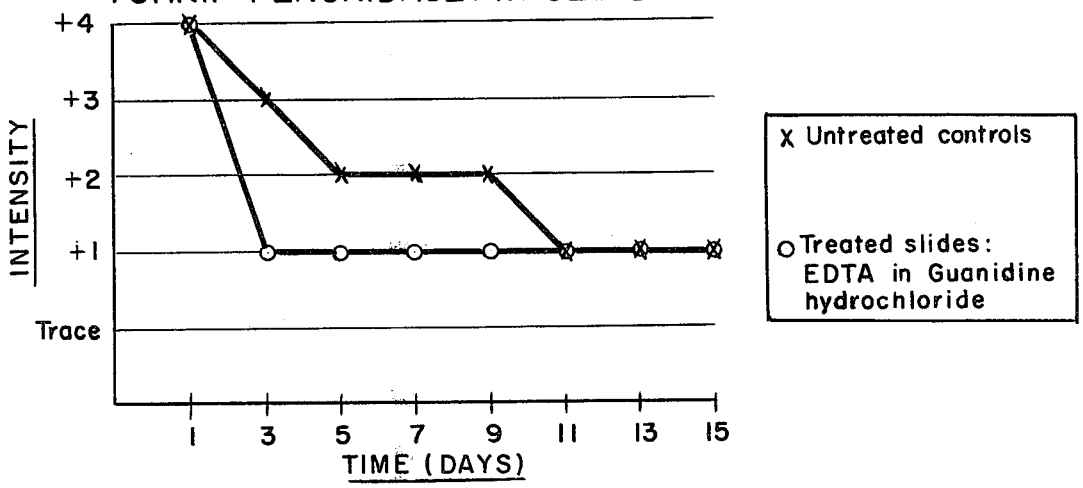
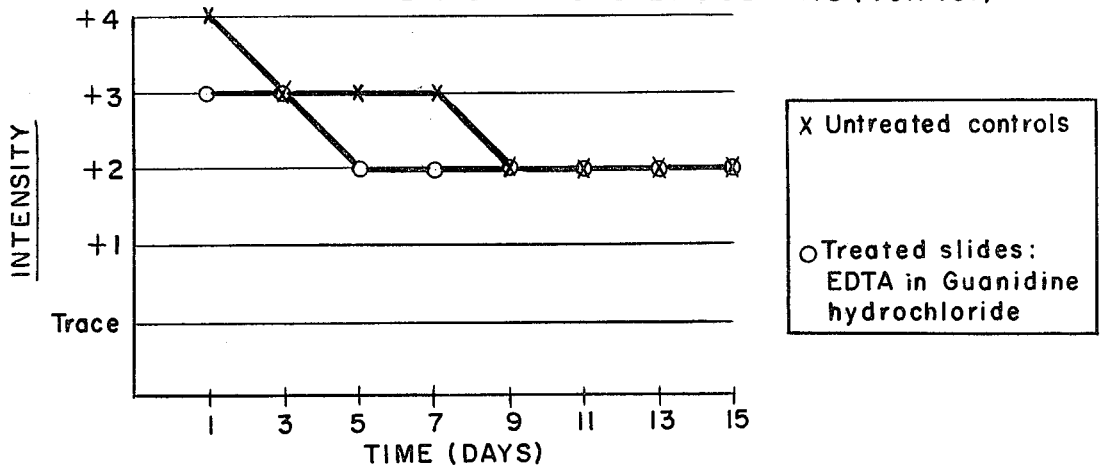

DIAGNOSTIC DEVICE FOR FECAL OCCULT BLOOD AND METHOD OF USE

The invention described herein was made in the course of work under a grant or award from the Department of Health, Education and Welfare.

CROSS REFERENCE TO RELATED APPLICATION

This is a continuation-in-part of Ser. No. 113,414 filed Jan. 18, 1980 (now abandoned).

BACKGROUND

This invention relates to a diagnostic test device for fecal occult blood utilizing guaiac as the test indicator. More particularly, this invention relates to a test matrix such as paper impregnated with guaiac together with a combination of substances which according to the invention prevent false-positive results in the presence of peroxidases.

A sensitive, specific and simple laboratory test for colorectal cancer is helpful in screening patients for early neoplastic lesions.

A test already available is the Hemoccult slide test for occult blood in stool (see U.S. Pat. No. 3,996,006). This simple, inexpensive laboratory test is capable of detecting blood in stool that may be related to an early cancerous lesion of the gastrointestinal tract. The test rationale which uses guaiacimpregnated paper as a test matrix is based on the phenolic oxidation of guaiac by hemoglobin in the presence of hydrogen peroxide. The production of a blue color on the test paper usually indicates the presence of blood. However, there is a 4 to 6% false positive reaction (i.e., positive test reaction without disease) as a result of non-hemoglobin interfering compounds present in the stool. It has been found that these interfering compounds are peroxidases ubiquitous to bacterial flora in the gut and in certain food sources. Each false-positive test may result in an exhaustive clinical investigation that is costly to the patient and time consuming for the physician. Aside the waste of money and manpower, the patient may be subjected to tremendous anxiety as the presence of blood in the feces may be an indication of cancer or other serious maladies.

In order to reduce the incident of interference by peroxidase in the guaiac test procedure for hemoglobin, it is a usual practice to prohibit a patient from eating vegetable products that contain peroxidase, e.g., potato, cabbage, onions, horseradish, etc. for several days. This gives time for possible interfering substances to be cleared from the body. However, indigenously present perioxidase (bacterial peroxidase) may still interfere with the test. Also patients may inadvertantly or otherwise ingest interfering substance containing vegetables notwithstanding instructions to avoid them.

The reaction of hemoglobin in fetal occult blood with guaiac in the presence of hydrogen peroxide, to give a blue color, is a known method for detection of the presence of blood as discussed above. This reaction takes advantage of the peroxidase activity of hemoglobin, which is similar to the reaction of peroxidase enzymes except that the peroxidase enzyme reaction is due to biochemical enzymatic activity while hemoglobin is not an enzyme. It is the recognition that peroxidase reacts with guaiac through enzymatic action while hemoglobin does not, that forms the basis of the present invention. By at least partially denaturing the protein that forms the peroxidase enzyme and removing the calcium and magnesium ions necessary for efficient peroxidase enzyme activity from the reaction mixture, one can eliminate the interfering effect of the peroxidase without practically affecting the hemoglobin.

It is therefor an object to avoid the problems inherent in prior art techniques by deactivating interfering peroxidase that may be present.

SUMMARY

The present invention provides an improvement in the diagnostic test technique for fecal occult blood which employs the reaction of guaiac with hemoglobin in the presence of peroxide to indicate the presence of hemoglobin by preventing false positive results. The improvement for preventing false-positive results in the presence of peroxidases comprises deactivating the peroxidase enzyme and removing the calcium and magnesium ions necessary for its efficient biochemical activity. This is preferably accomplished by cleaving the hydrogen bonds in the protein that forms the peroxidase enzyme thereby denaturing the peroxidase enzyme; and binding the calcium and/or magnesium ions with a chelating agent thereby reducing the efficiency of biochemical activity of the enzyme.

BRIEF DESCRIPTION OF THE DRAWING

The present invention will be more fully understood from the following description taken in conjunction with the accompanying drawing wherein:

FIG. 1 is a graph charting intensity against time in connection with 3:1 mixtures of turnip peroxidase in whole blood;

FIG. 2 is a graph charting intensity against time in connection with 1:1 mixtures of turnip peroxidase in whole blood; and FIG. 3 is a graph charting intensity against time in connection with 1:3 mixtures of turnip peroxidase in whole blood.

DESCRIPTION

The thrust of the present invention is the neutralization of the effect of peroxidase enzymes on the fecal occult blood test based on a color reaction of hemoglobin with guaiac in the presence of peroxide. This is in contradistinction to the usual procedure whereby mainly through dietary restrictions, it is attempted to eliminate the peroxidases from the sample.

In the presently preferred embodiments of the invention, the effect of peroxidase enzymes is neutralized by a combination of at least partially denaturing the enzyme proteins; and effectively removing the metal ions (calcium and magnesium) from the reaction mixture which the enzyme requires for efficient biochemical activity. The effective removal of the metal ions, which can be accomplished without physical removal by use of complexing agents, avoids the need for complete denaturization of the enzyme. Thus milder methods, unlikely to greatly effect any hemoglobin that may be present, can be used. Normal color development with hydrogen peroxide is thereafter accomplished.

Heating to about 100° C. and the use of strong acids are examples of two possible denaturing methods for the enzyme protein. These are not preferred, however, as heating feces results in obnoxious smells and both heating and the use of strong acids can cause damage to any hemoglobin present. The most preferred denaturing method is the use of an effective amount of a compound that will cleave hydrogen bonds in the protein that forms the peroxidase enzyme. This will at least partially attenuate biochemical activity of the enzyme. The effective removal of calcium and magnesium ions from the reaction by complexing with a chelating agent further attenuates the biochemical activity of the enzyme to a point where, for practical purposes, the interfering effect of the peroxidase is eliminated. This combination of steps allows the use of moderate amounts of reagents and mild conditions to avoid effect on the hemoglobin to be tested.

Guaiac containing test matrices suitable for the practice of the fecal occult blood determination tests of the type over which the present invention is an improvement are known. One such device, a guaiac impregnated paper, is sold under the trademark Hemoccult and described in U.S. Pat. No. 3,996,006 referred to hereinabove. It is contemplated in the preferred embodiments hereof that the materials for neutralizing the effect of the peroxidase can be used in conjunction with known test matrices and may be applied to the test matrix either before or after the test sample is applied. For ease of application, the compunds are dissolved in a suitable solvent, most usually water, and aliquoted amounts applied to the test matrix.

Suitable compounds for at least partially denaturing the enzyme protein by cleaving hydrogen bonds include the soluble (water) salts of guanidine, urea and salicylic acid. The preferred compound is guanidine hydrochloride. As noted above, heating or the use of strong acids has possible undesirable side effects that are difficult or impossible to control.

Chelating agents that have been found suitable to sufficiently remove the metal ions necessary for effective enzyme action include ethylenediamine tetraacetic acid (EDTA) and ethyleneglycol tetraacetic acid (EGTA).

Effective amounts of the compound and chelating agent are utilized in the guaiac containing test matrix. For example, a 3 to 6 molar solution of guanidine hydrochloride in water can be used with a 10–100 millimolar solution of EDTA in water. These two solutions are combined in equal volume to form a test reagent solution and then added in an aliquot portion to the guaiac test matrix. If the test reagent solution is added before the test sample, the water can be removed so that the test matrix can be stored for receipt of a test sample at a subsequent time and location (e.g. for a doctor's office or hospital use). Alternatively, a test matrix to which a sample has already been applied can subsequently have the test reagent solution added. In either case, after a suitable reaction period, the test can proceed in a usual manner with the development of possible color using hydrogen peroxide.

At concentrations lower than about 3 moles/l, guanidine hydrochloride shows no effect while in concentrations at about 6 moles, guanidine hydrochloride undesirably crystallizes out on paper when the test matrix used is guanidine impregnated paper. In concentrations below 10 millimolar for EDTA, the desirable results in the invention are not shown and at concentrations at above 100 millimoles/l for EDTA, there is no demonstrated increase in effect.

A preferred embodiment of the invention involves the use of guaiac impregnated paper such as the Hemoccult slide to which is added EDTA and guanidine hydrochloride such that the guaiac impregnated paper contains 0.25 millimoles of EDTA and 0.15 millimoles of guanidine hydrochloride. This can be accomplished by combining equal solutions of 3 molar guanidine hydrochloride and a 100 millimolar solution of EDTA and depositing the 25 microliters of the combined solution on the Hemoccult slide.

Where the test solution is to be added to the paper before the sample, the solution containing guanidine hydrochloride and EDTA can be simply combined with the guaiac test matrix in the case where guaiac is in a liquid test matrix, or it can be sprayed or rolled on to a guaiac impregnated paper in the instance where the test matrix is paper. If added after the test sample, the test solution will necessarily be sprayed or dropped onto the matrix.

The following examples are intended to illustrate the invention without limiting the same in any manner. These examples report results of the embodiment wherein the test reagent solution is added to the test matrix before the sample.

In all the examples that follow, color intensity is scored as follows:
Negative—no color response
Trace—color response barely visible to naked eye
+1—slight color response
+2—moderate color response
+3—strong color response
+4—very strong color response

EXAMPLE 1

Effects of EDTA and Guanidine hydrochloride on vegetable and hemoglobin peroxidase activity on Hemoccult slides.

|  | 0.36 mg/ml Horseradish Peroxidase | 0.36 mg/ml Powdered Hemoglobin | Control Slides: no peroxidase added |
|---|---|---|---|
| Control I non-treated slides | +3 | +4 | neg. |
| Control II slides treated with H₂O | +3 | +3 | neg. |
| 6M Guanidine hydrochloride | +4 | +4 |  |
| 10mM EDTA | +3 | +4 | neg. |
| 10mM EDTA in 6M Guanidine hydrochloride | Trace | +4 | neg. |
| 100mM EDTA | +2 | +3 | neg. |
| 100mM EDTA in 6M Guanidine hydrochloride | Trace | +3 | neg. |

Applications of 25 μl of the treatment solutions were dried on slides, followed by the applications of 25 μl of vegetable peroxidase and hemoglobin (Hb). The slides were developed 17–21 hours after applications.

EXAMPLE 2

Effects of EDTA plus Guanidine Hydrochloride on vegetable peroxidases and hemoglobin peroxidase activity on Hemoccult slides.

|  | 0.36 mg/ml Powdered Hemoglobin | 0.36 mg/ml Whole Blood Lysate | Turnip Peroxidase Crude Extract (1 mg/ml) | | 0.36 mg/ml Horseradish Peroxidase |
|---|---|---|---|---|---|
|  |  |  | Undiluted | Diluted |  |
| Control I | +4 | +4 | +4 | +3 | +3 |

-continued

Effects of EDTA plus Guanidine Hydrochloride on vegetable peroxidases and hemoglobin peroxidase activity on Hemoccult slides.

| | 0.36 mg/ml Powdered Hemoglobin | 0.36 mg/ml Whole Blood Lysate | Turnip Peroxidase Crude Extract (1 mg/ml) | | 0.36 mg/ml Horseradish Peroxidase |
|---|---|---|---|---|---|
| | | | Undiluted | Diluted | |
| non-treated slides Control II | +3 | +4 | +4 | +3 | +3 |
| slides treated with H$_2$O | | | | | |
| 10mM EDTA in 6M Guanidine HCl | +4 | +4 | +1 | neg. | Trace |
| 100mM EDTA in 6M Guanidine HCl | +3 | +4 | Trace | neg. | Trace |

Applications of EDTA and water treatments (25 μl/slide window) were dried on slides prior to the 25 μl applications of peroxidases and hemoglobin. The slides were developed 17–21 hours after applications.

EXAMPLE 3

Whole Blood and Turnip Peroxidase Volume: Volume Mixtures: Effects of EDTA plus Guanidine Hydrochloride.

| Water (Control) | |
|---|---|
| Not Treated Water | Treated Water |

| | Inhibition of vegetable peroxidases by EDTA plus Guanidine Hydrochloride on Hemoccult slides. | | | | | | | | |
|---|---|---|---|---|---|---|---|---|---|
| | Horseradish Peroxidase 0.36 mg/ml | | Turnip Peroxidase Undiluted (1 mg/ml) | | Turnip Peroxidase Diluted 3:1 with water | | Powdered Hemoglobin 0.36 mg/ml | | Whole Blood lysate(Hb) 0.36 mg/ml | |
| | Treated* | Untreated | Treated* | Untreated | Treated* | Untreated | Treated* | Untreated | Treated* | Untreated |
| Color Intensity | Trace | +4 | Trace | +3 | neg. | +2 | +3 | +3 | +3 | +3 |

*Treated with 10 mM EDTA in 6M Guanidine hydrochloride.

| Volume ratio | Turnip Peroxidase | | | Volume ratio | Turnip Peroxidase | | |
|---|---|---|---|---|---|---|---|
| | 1 | 2 | 3 | | 1 | 2 | 3 |
| 1 | +2 | +3 | +3 | 1 | Neg. | Neg. | Trace |
| 2 | +2 | | | 2 | Neg. | | |
| 3 | +1 | | | 3 | Neg. | | |

| Whole Blood Lysate (Control) | | | | | | | |
|---|---|---|---|---|---|---|---|
| Not Treated Whole Blood Lysate | | | | Treated Whole Blood Lysate | | | |
| Volume ratio | Water | | | Volume ratio | Water | | |
| | 1 | 2 | 3 | | 1 | 2 | 3 |
| 1 | +1 | Trace | Trace | 1 | +2 | +1 | Trace |
| 2 | +1 | | | 2 | +2 | | |
| 3 | +1 | | | 3 | +2 | | |

| Whole Blood Lysate With Turnip Peroxidase | | | | | | | |
|---|---|---|---|---|---|---|---|
| Not Treated Whole Blood Lysate | | | | Treated Whole Blood Lysate | | | |
| Volume ratio | Turnip Peroxidase | | | Volume ratio | Turnip Peroxidase | | |
| | 1 | 2 | 3 | | 1 | 2 | 3 |
| 1 | +1 | +2 | +2 | 1 | +1 | +1 | Trace |
| 2 | +2 | | | 2 | +1 | | |
| 3 | +3 | | | 3 | +2 | | |

Undiluted turnip peroxidase extract and 0.06 mg Hb/ml whole blood lysated were combined in the volume: volume ratios indicated of which 25 μl were applied on untreated and treated Hemoccult II slides lot 7087 (10/81). Hemoccult slides were treated with 25 μl 0.01 M EDTA in 6 M Guanidine hydrochloride.

EXAMPLE 4

Whole blood and powdered hemoglobin in stool specimens: Time study with EDTA plus Guanidine Hydrochloride on Hemoccult slides.

| | Powdered Hemoglobin 0.075 gm Hb/ 100 gm Specimen | | Whole Blood Lysate 0.100 gm Hb/ 100 gm Specimen | |
|---|---|---|---|---|
| Time Days | Untreated | Treated | Untreated | Treated |
| 1 | +2 | +2 | +3 | +3 |
| 4 | +2 | +2 | +3 | +3 |
| 5 | +2 | +2 | +3 | +3 |
| 7 | +2 | +2 | +3 | +3 |
| 8 | +2 | +2 | +3 | +3 |
| 11 | +2 | +2 | +3 | +3 |
| 12 | +2 | +2 | +3 | +3 |
| 14 | +2 | +1 | +3 | +3 |
| 15 | +2 | +1 | +3 | +3 |

Stool specimens, negative for occult blood, were "spiked" with powdered hemoglobin and whole blood. Hemoccult slides were treated with 25 μl 0.01 M EDTA in 6 M Guanidine hydrochloride per slide window, dried and spotted with 25 μl hemoglobin and whole blood. The slides were stored in the dark for times indicated.

EXAMPLE 5

Hemoccult slides were treated with 10 mM EDTA in 6 M Guanidine hydrochloride, dried and stored in the dark for one month. After one month, 25 μl of hemoglobin and vegetable peroxidase were applied to the slides. The slides were developed 17–21 hours after application of hemoglobin or peroxidase.

EXAMPLE 6

Whole Blood and Turnip Peroxidase Volume: Volume mixtures: Effectiveness of EDTA plus Guanidine hydrochloride with storage time on Hemoccult slides.

FIG. 1. Turnip Peroxidase: Whole Blood = 3:1 (vol:-vol).

FIG. 2. Turnip Peroxidase: Whole Blood = 1:1 (vol:-vol).

FIG. 3. Turnip Peroxidase: Whole Blood — 1:3 (vol:-vol).

Hemoccult slides were treated with 25 μl 10 mM EDTA in 6 M Guanidine hydrochloride per window and dried. Mixtures of 0.06 mg Hb/ml whole blood and undiluted turnip peroxidase extract were prepared volume:volume and 25 μl per window were applied to treated and untreated slides. The slides were stored in the dark at room temperature and developed on days indicated.

EXAMPLE 7

Hemoglobin and vegetable peroxidases: Effectiveness of EDTA plus Guanidine hydrochloride with storage time on Hemoccult slides.

|  | 10 mM EDTA in 6 M Guanidine hydrochloride | 1 month | 2 months | 3 months | 4 months | 5 months | 6 months | 7 months |
|---|---|---|---|---|---|---|---|---|
| 0.36 mg/ml Horseradish Peroxidase | not treated | +4 | +4 | +4 | +4 | +4 | +4 | +4 |
|  | treated | Trace | Trace | Trace | neg. | neg. | neg. | +1 |
| Undiluted extract Turnip Peroxidase | not treated | +3 | +3 | +4 | +3 | +3 | +3 | +2 |
|  | treated | Trace | neg. | Trace | Trace | Trace | Trace | Trace |
| Diluted extract 3:1 water: Turnip Peroxidase | not treated | +2 | +3 | +3 | — | — | — | — |
|  | treated | Trace | neg. | Trace | — | — | — | — |
| 0.36 mg/ml Powdered Hemoglobin | not treated | +3 | +3 | +3 | +3 | +3 | +3 | +3 |
|  | treated | +3 | +3 | +3 | +3 | +3 | +3 | +3 |
| 0.36 mg/ml Whole Blood Lysate | not treated | +3 | +3 | +4 | +3 | +3 | +3 | +3 |
|  | treated | +3 | +3 | +4 | +3 | +3 | +3 | +3 |

Hemoccult slides were treated with 25 µl 10 mM EDTA in 6 M Guanidine hydrochloride, dried and stored in the dark at room temperature. At one month intervals, 25 µl hemoglobin or vegetable peroxidase were applied to the slides. The slides were developed at 17–21 hours after application of the hemoglobin or peroxidase.

The following examples illustrate the second preferred embodiment wherein the test reagent solution is added to the test matrix at a time subsequent to the application of the sample. This is presently more preferred because it avoids storage-life problems and permits use of readily commercially available test materials.

Basically, guanidine hydrochloride and EDTA are applied to the fecal occult blood test matrix prior to the normal color development procedure by addition of hydrogen peroxide. This simple modification in technique effectively inhibits peroxidase activity present in the stool specimen and is applicable to any test matrix, regardless of previous chemical impregnation, size or shape of the test matrix.

TEST PROCEDURE

One hundred micro-liters (100 µl) or approximately 2 drops of a solution of guanidine hydrochloride-EDTA (0.01 M EDTA in 3 M guanidine hydrochloride) are applied to the test window of the fecal occult blood test matrix. After approximately 2½ hours of pretreatment at room temperature, the color developing process is completed by the usual procedure involving the addition of 2 drops of hydrogen peroxide to the slide. A pretreatment period before addition of the peroxide of 2 to 3 hours is required to effectively inhibit peroxidase activity.

The following examples illustrate the effectiveness of peroxidase inhibition by a solution of guanidine hydrochloride (3 M) and EDTA (0.01 M):

EXAMPLE 8

Application of Guanidine Hydrochloride-EDTA Prior to Color Development Process

| Time (hours) (pretreatment prior to addition of peroxide reagent) | Horseradish Peroxidase (0.36 mg/ml) | Whole Blood Lysate (0.36 mgHb/ml) | Powdered Hb (0.36 mg/ml) |
|---|---|---|---|
| ½ | +4 | +4 | +4 |
| 1½ | +3 | +4 | +4 |
| 2 | +2 | +4 | +4 |
| 2½ | +1 | +4 | +4 |
| 3 | Trace | +4 | +4 |
| 3½ | Trace | +4 | +4 |
| 4 | Neg. | +4 | +4 |
| 4½ | Neg. | +4 | +4 |

EXAMPLE 9

Effect of Peroxidase Activity on Color Development Without Prior Treatment with Guanidine Hydrochloride and EDTA

| Time | Horseradish Peroxidase (0.36 mg/ml) | Whole Blood Lysate (0.36 mg/ml) | Powdered Hb (0.36 mg/ml) |
|---|---|---|---|
| ½ | +4 | +4 | +4 |
| 1½ | +4 | +4 | +4 |
| 2 | +4 | +4 | +4 |
| 2½ | +4 | +4 | +4 |
| 3 | +4 | +4 | +4 |
| 3½ | +4 | +4 | +4 |
| 4 | +4 | +4 | +4 |
| 4½ | +4 | +4 | +4 |

Similar results are obtained using EGTA as a chelating agent and urea or salicylic acid to cleave protein hydrogen bonds.

The above is intended to be illustrative of presently preferred embodiments, and not in any way restrictive on the scope of the invention.

What is claimed is:

1. In a process for determining the presence of fecal occult blood in a test sample using a test matrix containing guaiac, the improvement for preventing false-positive results in the presence of peroxidase enzymes comprising the steps of at least partially denaturing the protein forming the peroxidase enzymes with an effective amount of a compound from the group consisting of soluble salts of guanidine, urea and salicyclic acid to attenuate enzymatic activity; and effectively removing from reaction with the peroxidase enzymes, magnesium and/or calcium ions, necessary for efficient biochemical activity of the peroxidase enzyme.

2. The process of claim 1 wherein the ions are effectively removed from reaction with the peroxidase enzymes with an effective amount of a chelating agent.

3. The process of claim 2 wherein the test matrix is paper.

4. The process of claim 2 wherein the chelating agent is selected from EDTA and EGTA.

5. The process of claim 4 further comprising the steps of adding the compound and the chelating agent to the matrix and thereafter supporting the test sample on the matrix.

6. The process of claim 4 further comprising the steps of adding the test sample to the matrix and thereafter adding the compound and chelating agent to the matrix.

7. In a test kit for the process of claim 1, the improvement comprising a solution for application to the test matrix in a predetermined unit volume and containing an effective amount, per predetermined unit volume, of (a) a compound from the group consisting of soluble salts of guanidine, urea and salicyclic acid that cleaves protein hydrogen bonds, to at least partially denature peroxidase enzymes in the test sample and (b) of a chelating agent that binds calcium and magnesium ions to insure the effective removal of calcium and magnesium from reaction with peroxidase enzymes in the test sample.

8. Test kit of claim 7 wherein the chelating agent is EDTA or EGTA.

9. Test kit of claim 7 wherein the test matrix is paper.

10. Diagnostic test device for false-positive test free testing for fecal occult blood in the presence of interfering peroxidase enzyme, in accordance with the process of claim 1, comprising a test matrix of paper impregnated with an effective amount of guaiac, a compound from the group consisting of soluble salts of guanidine, urea and salicyclic acid that cleaves protein hydrogen bonds thereby to denature the protein forming the enzyme, and a chelating agent that binds calcium and/or magnesium ions thereby to remove the ions from reaction with the enzyme.

11. The device of claim 10 wherein said compound is a soluble salt of guanidine and said chelating agent is EDTA.

12. The test device of claim 10 wherein there is present about 0.25 millimoles EDTA and about 0.15 millimoles guanidine hydrochloride.

* * * * *

UNITED STATES PATENT AND TRADEMARK OFFICE
CERTIFICATE OF CORRECTION

PATENT NO. : 4,333,734

DATED : June 8, 1982

INVENTOR(S) : Martin Fleisher

It is certified that error appears in the above-identified patent and that said Letters Patent is hereby corrected as shown below:

Col. 1, Lines 5, 6 and 7 - delete these lines.

Signed and Sealed this

Twenty-seventh Day of March 1984

[SEAL]

Attest:

GERALD J. MOSSINGHOFF

Attesting Officer

Commissioner of Patents and Trademarks